(12) United States Patent
Hardert et al.

(10) Patent No.: US 8,246,568 B2
(45) Date of Patent: Aug. 21, 2012

(54) HEMODIALYSIS CATHETER WITH THROMBUS REMOVING DEVICE

(75) Inventors: Michael W. Hardert, Bloomington, IN (US); Michael R. Kurrus, Ellettsville, IN (US); Amy Lee Hruska, Indianapolis, IN (US); Tyson L. Rugenstein, Camby, IN (US); Elizabeth A. Theobald, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 416 days.

(21) Appl. No.: 12/551,030

(22) Filed: Aug. 31, 2009

(65) Prior Publication Data

US 2011/0054379 A1 Mar. 3, 2011

(51) Int. Cl.
*A61M 37/00* (2006.01)
*A61M 31/00* (2006.01)

(52) U.S. Cl. .................. 604/6.01; 604/6.16; 604/508

(58) Field of Classification Search ................ 604/4.01, 604/5.01, 6.01, 6.09, 6.1, 6.16, 21, 22, 96.01, 604/264, 500, 503, 508; 606/159
See application file for complete search history.

(56) References Cited

U.S. PATENT DOCUMENTS

| | | | |
|---|---|---|---|
| 4,772,268 A | 9/1988 | Bates | |
| 5,509,897 A | 4/1996 | Twardowski et al. | |
| 5,989,213 A | 11/1999 | Maginot | |
| 6,319,242 B1 * | 11/2001 | Patterson et al. | 604/508 |
| 6,966,914 B2 | 11/2005 | Abe | |
| 2003/0104073 A1 * | 6/2003 | Johansson et al. | 424/600 |
| 2006/0259118 A1 | 11/2006 | Pal et al. | |

OTHER PUBLICATIONS

Cook Incorporated; "Gunther Tulip Vena Cava Filter Retrieval Set for Jugular Vein Approach"; Instructions for Use Optional Retrieval Procedure; *Cook Incorporated 2003*, T-TULRET1003; 5 pgs.

* cited by examiner

*Primary Examiner* — Tatyana Zalukaeva
*Assistant Examiner* — Philip R Wiest
(74) *Attorney, Agent, or Firm* — Brinks Hofer Gilson & Lione

(57) ABSTRACT

The present disclosure provides apparatus and methods for removing thrombus outside of a hemodialysis. The hemodialysis catheter comprises an elongate shaft comprising a plurality of lumens. A first lumen has a first distal port. The first lumen is configured for the flow of a fluid in a first direction. A second lumen has a second distal port proximal to the first distal port. The second lumen is configured for the flow of the fluid in a second direction opposite to the first direction. A third lumen has a third distal port proximal to the second distal port. An elongate device is disposed through the third lumen. The elongate device has an operable member on a distal end or a device to connect to an operable member disposed on the elongate shaft. The operable member is configured to engage and remove thrombus from an exterior surface on the elongate shaft.

11 Claims, 3 Drawing Sheets

HEMODIALYSIS CATHETER WITH THROMBUS REMOVING DEVICE

BACKGROUND

The present disclosure relates generally to apparatus and methods for catheters, and more specifically, for a hemodialysis catheter with thrombus removing device.

Catheters have been introduced as a minimal invasive device in many medical applications for temporary catheterization such as clot aspiration and long term catheterization such as hemodialysis. Hemodialysis catheters usually stay in the subject body for extended periods of time (e.g. several weeks or more) to withdraw fluid from the body for processing and simultaneously introduce processed fluid back into the body. Although hemodialysis catheters are minimally invasive, they are foreign to the body and may cause an inflammatory reaction. The reaction may introduce thrombus around the surface of hemodialysis catheters especially on the catheter tip. The thrombus may obstruct or even completely block the fluid flow in the hemodialysis catheters, which will result in a low blood flow rate and insufficient hemodialysis.

One problem that exists with the current devices and procedures is they will interfere with the ongoing hemodialysis treatment. In addition, thrombus will cause inconsistent performance of hemodialysis catheter. Therefore, it would be desirable to provide an apparatus and method for removing thrombus during the treatment to ensure the consistent performance of hemodialysis catheters.

Various devices and procedures are known for removing thrombus and keep the patency of hemodialysis catheters. A device such as a J-tipped guide wire or a biopsy brush can be passed through the obstructed hemodialysis catheter to remove thrombus from the lumens of the catheter. Thrombolytic agents can also be infused into the catheter to remove thrombus from the lumens. External snares have also been used to remove thrombus from the outside of the catheter. However, the advance of and manipulation of an external snare is difficult and time consuming.

SUMMARY

The present disclosure provides apparatus and methods for removing thrombus outside of a hemodialysis catheter by providing a third lumen with an operable member in the hemodialysis catheter.

One embodiment of the hemodialysis catheter comprises an elongate shaft comprising a plurality of lumens. A first lumen of the plurality of lumens has a first distal port. The first lumen is configured for the flow of a fluid in a first direction. A second lumen of the plurality of lumens has a second distal port proximal to the first distal port. The second lumen is configured for the flow of the fluid in a second direction opposite to the first direction. A third lumen of the plurality of lumens has a third distal port proximal to the second distal port. An elongate device is disposed through the third lumen. The elongate device has an operable member on a distal end thereof. The operable member is configured to engage and remove thrombus from an exterior surface on the elongate shaft.

In one embodiment, the operable member comprises an elongate shaft with a loop disposed on the distal end thereof, the loop is positioned so as to encircle the hemodialysis catheter.

In another embodiment, the operable member comprises an elongate shaft with a rigid curve member disposed on the distal end thereof, the curve member is positioned so as to enclose at least a portion of circumference the hemodialysis catheter.

A method to use the above embodiment of the hemodialysis catheter for removing thrombus or clots during a hemodialysis treatment includes providing a hemodialysis catheter having (i) an elongate shaft comprising a plurality of lumens; (ii) a first lumen of the plurality of lumens having a first distal port; (iii) a second lumen of the plurality of lumens having a second distal port proximal to the first distal port; (iv) a third lumen of the plurality of lumens having a third distal port proximal to the second distal port; and (v) an elongate device disposed through the third lumen, the elongate device having an operable member on a distal end thereof, the operable member configured to engage and remove thrombus from an exterior surface on the elongate shaft. An operator advances the operable member distally from the third distal port to a location near the first distal port and/or the second distal port. In particular, the operator may manipulate the operable member to break up the thrombus around the first distal port and/or the second distal port.

BRIEF DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION OF THE PREFERRED EMBODIMENTS

In the present application, the term "proximal" refers to a direction that is generally toward a physician during a medical procedure, while the term "distal" refers to a direction that is generally toward a target site within a patient's anatomy during a medical procedure.

Figure 1:
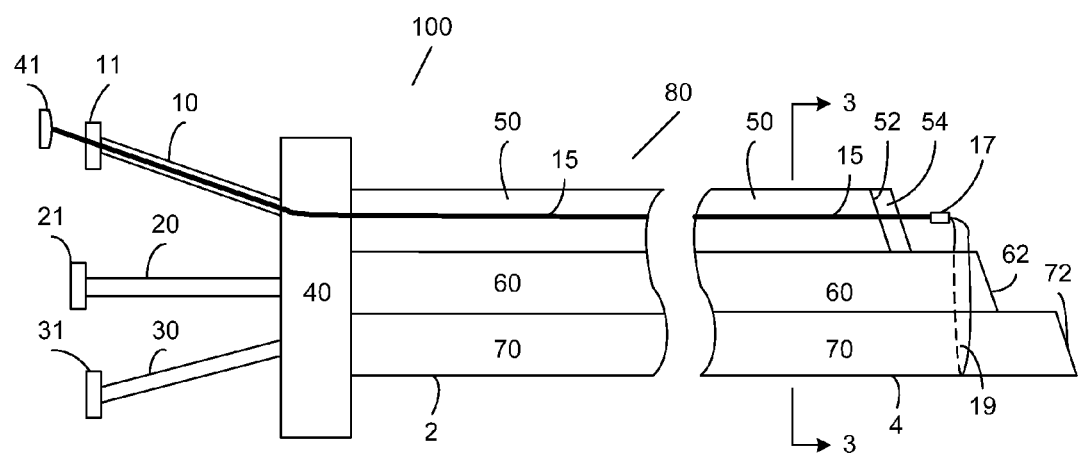
FIG. 1 is a side view of a first embodiment of a three-lumen hemodialysis catheter with a loop at an advanced position.
Figure 2:
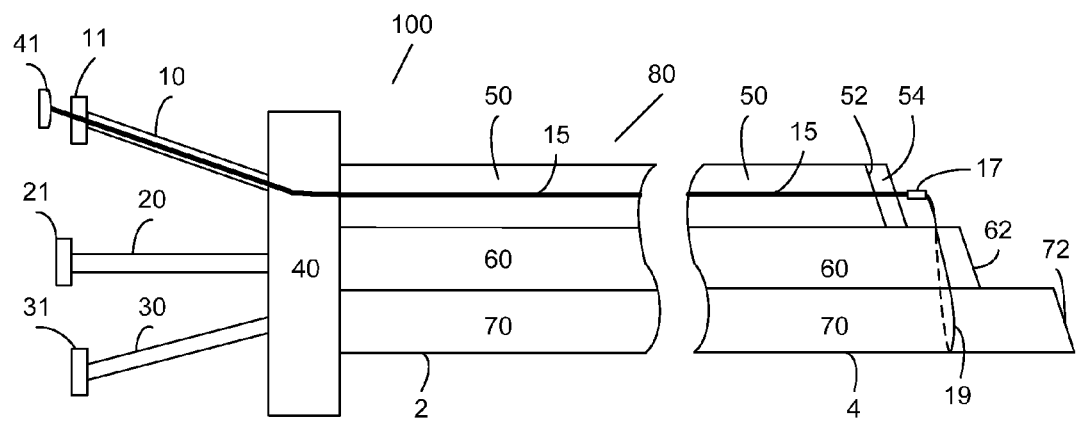
FIG. 2 is a side view of the three-lumen hemodialysis catheter of FIG. 1 with a twisted loop at a retracted position.
Figure 3:
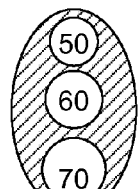
FIG. 3 is a cross section view of the first embodiment of the three-lumen hemodialysis catheter taken along line 3-3 in FIG. 1.

Referring now to FIGS. 1-3, a first embodiment of a three-lumen catheter 100 for hemodialysis treatment is described. The three-lumen catheter 100 comprises an elongate shaft 80 comprising three lumens, a fitting 40, and an operable member 19, as shown in FIG. 1. The hemodialysis catheter 100 has proximal region 2 distal region 4 respectively. The three lumens each has a distal port opening in the distal region of the hemodialysis catheter 100. A first lumen 70 has a first distal port 72. The first lumen 70 may be configured for the flow of a fluid in a first direction during a hemodialysis treatment. A second lumen 60 has a second distal port 62 proximal to the first distal port 72. The second lumen 60 may be configured for the flow of the fluid in a second direction opposite to the first direction during a hemodialysis treatment. A third lumen 50 has a third distal port 52 proximal to the second distal port 62. The third distal port may have a flap-like or valve-like cover 54 to prevent clotting thereon. The cover 54 is movable. The cover 54 may comprise a plastic part over a metal frame, and the plastic part may be heparin coated to prevent clot formation. An elongate device 15 is disposed through the third lumen 50. The elongate device 15 may have an operable member 19 on a distal end thereof. The operable member 19 is configured to engage and remove thrombus or other undesirable material from an exterior surface on the elongate shaft 80 especially around the first distal port 72 and the second distal port 62. The figures shown are for illustration purpose only and not to scale. The actual catheters comply with the standard manufacture and catheter design procedures.

The operable member 19 may be connected with the elongate device 15 permanently or temporarily through a device 17. The operable member 19 may also be removed from the hemodialysis catheter 100 for cleaning or other purposes. The operable member 19 may be an elastic loop as shown in FIG. 1. The operable member 19 may comprise other devices such as adjustable balloon, brushes or snare with expandable bristles configured for removing clots. The removed clots may be further removed from the blood vessel through one of the three lumens.

The elongate device 15 may be pulled back as shown in FIG. 2. The operable member 19 may be manipulated to fit tightly outside the first lumen 70, the second lumen 60, or both the first lumen 70 and the second lumen 60. The elongate device 15 may be pushed and pulled along the elongate shaft 80 while manipulating the opening of the operable member 19. This action tends to break up and remove any thrombus from the outside of the catheter.

The elongate shaft 80 may be formed from one or more semi-rigid polymers. For example, the shaft may be manufactured from polyurethane, polyethylene, tetrafluoroethylene, polytetrafluoroethylene, fluorinated ethylene propylene, nylon, PEBAX or the like.

The operable member 19 may be manufactured from a snare material, e.g., shape memory material or self-sustaining medical grade material, which may be suitable to make a snare. In this case, the operable member 19 may be a snare such as the Günther Tulip™ Vena Cava Filter Retrieval Set manufactured by Cook Medical Inc. The snare may be advanced as in FIG. 1 or retracted as in FIG. 2.

FIG. 3 shows a cross section view of the elongate shaft 80 taken along line 3-3. The first lumen 70 may have the largest cross section area among the three lumens. The cross section area of the second lumen 60 may be less or equal than the cross section area of the first lumen 70. The third lumen 50 may have the smallest cross section area among the three lumens. The third lumen 50 may have a cross section area equal to that of the other two lumens. The cross sections of the three lumens may be circular or other shapes such as oval.

As shown in FIG. 1 and FIG. 2, the fitting 40 may be used to fix the hemodialysis catheter 100 on a patient or other subjects as described in the U.S. Pat. No. 4,772,268. The fitting 40 may include adapters to connect tubes 20 and 30 to the second lumen 60 and the first lumen 70 respectively. There are also adapters 21 and 31 on the tubes 20 and 30. The adapters 21 and 31 may be used to connect the tubes 20 and 30 to other apparatus during a hemodialysis treatment. The elongate device 15 maybe connected to a tube 10. The tube 10 may be connected to a control device through an adapter valve 11.

During a hemodialysis treatment, when the fluid flow is not as fast as desired, an operator such as a doctor or a nurse may use the above described three lumen catheter 100 to remove the accumulated clot or thrombus around the outside surface of the elongate shaft 80. In the first step, the operator may advance elongate device 15 with the operable member 19 distal to the first distal port or the second distal port. The operable member 19 may be in a closed state or a resting state while advancing through the third lumen 50.

In the second step, the operator may manipulate the operable member 19 according to a medical imaging device in the device 17. The operator may further manipulate the operable member with the help of other medical imaging device such as a real time ultrasound imaging system. The operable member 19 may be manipulated in an open state or working state during this step.

In the third step, the operator may push and pull the elongate device 15 with the operable member 19 to break thrombus around the first distal port or the second distal port. The operator may apply other material such as urethane on the operable member 19 to improve the performance of the operable member. The operator may further apply other material such as urethane within the third lumen 50 or on the elongate device 15 to maintain the patency of the third lumen 50.

In the fourth step, the operator may control the operable member 19 to collect the broken thrombus and remove it from the blood vessel by using suck with a vacuum generating device connected to the third lumen 50. The operable member 19 may be manipulated to a holding state to hold the broken thrombus during this step.

In the final step, the operator may remove the elongate device 15 with the operable member 19 for cleaning or other purposes. Or if the operable member 19 is to be retracted into the lumen, inside of the catheter and remained there until it needed to be used again, a plastic sleeve may be utilized to encompass the outer portions of the operable member 19 and the elongate device 15 to ensure sterility when the operator is moving the snare back and forth. The plastic sleeve may also be configured to cover other parts of the catheter to ensure sterility. The operator may close the flap-like or valve-like cover 54 after the elongate device 15 is removed from the three-lumen hemodialysis catheter 100.

Figure 6A:
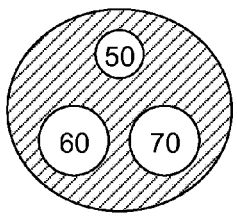
FIG. 6A is a cross section view of a second embodiment of the three-lumen hemodialysis catheter taken along line 6-6 in FIG. 4.
Figure 6B:
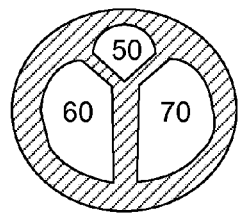
FIG. 6B is a cross section view of a second embodiment of the three-lumen hemodialysis catheter taken along line 6-6 in FIG. 4.
Figure 4:
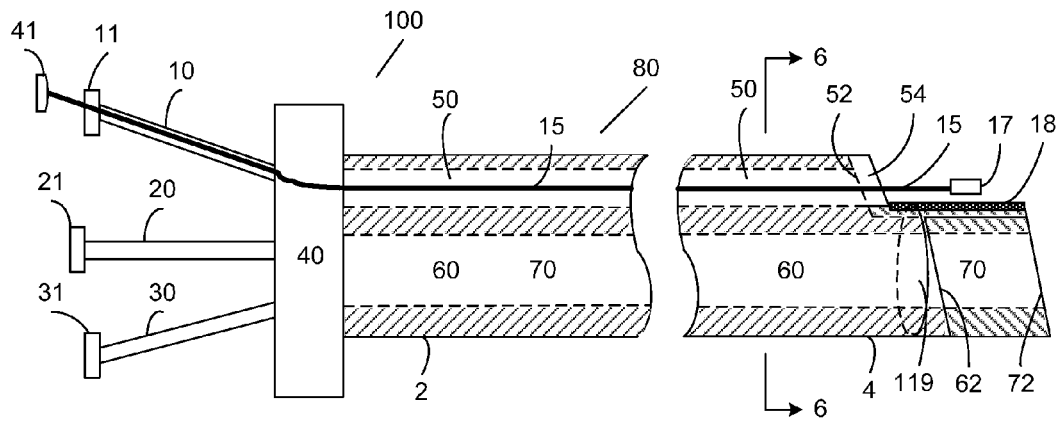
FIG. 4 is a side view of a second embodiment of a three-lumen hemodialysis catheter with a rigid hoop at a retracted position.
Figure 5:
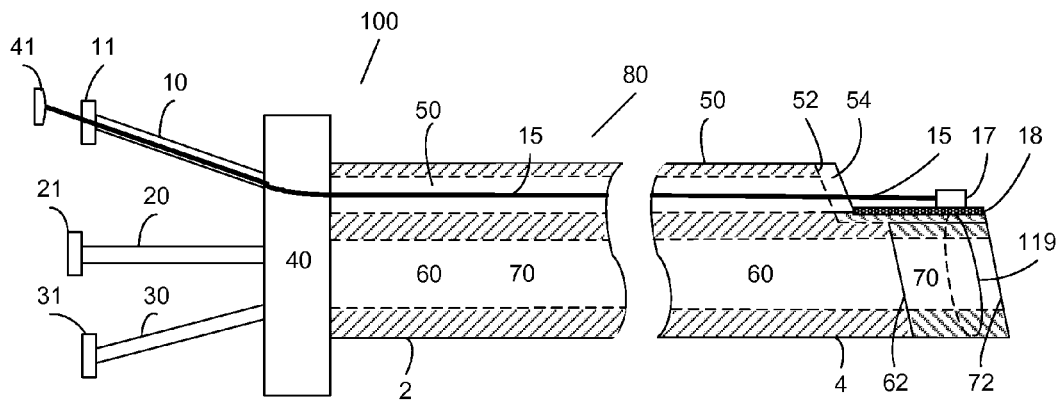
FIG. 5 is a side view of the three-lumen hemodialysis catheter of FIG. 4 with a rigid hoop at an advanced position.

Referring now to FIGS. 4-6, a second embodiment of the three-lumen catheter 100 for hemodialysis treatment is described. There are two differences between the first embodiment and the second embodiment. The first difference between the first embodiment and the second embodiment is the cross section areas of the elongate shaft 80 and the three lumens. The cross section of the elongate shaft 80 is a circle in the second embodiment. The first lumen 70 and the second lumen 60 have similar cross section areas. The third lumen 50 has a cross section area smaller than that of the first lumen 70 and the second lumen 60.

Another difference between the first embodiment and the second embodiment is the operable member 119 is not permanently attached to the elongate device 15. The operable member 119 may be a hoop or a rigid curve member disposed about at least a portion of the circumference of the catheter 100 in the distal region 4. The operable member 119 may be attached to the outside of the elongate shaft 80 through a connector device 18. Specifically, the connector device 18 may be a hook device fixed to one of the three lumens. The connector device 18 may be a groove on the outside surface of the catheter. The connector device 18 may be combined with the flap-like or valve-like cover 54. The elongate device 15 may connect to the operable member 119 directly or through a device 17. The elongate device 15 may connect to the connector device 18 directly or through a device 17.

During a hemodialysis treatment, when the fluid flow is not as fast as desired, an operator such as a doctor or a nurse may use the above described three lumen catheter 100 to remove the accumulated clot or thrombus around the outside surface of the elongate shaft 80. In the first step, the operator may advance elongate device 15 in the third lumen 50 distal toward the first distal port 72 or the second distal port 62.

In the second step, the operator may connect the elongate device 15 to the operable member 119 directly or through the device 17 or connector device 18. The operable member 119 may be activated to a working state after being connected.

In the third step, the operator may manipulate the operable member according to a medical imaging device in the device 17. The operator may further manipulate the operable member with the help of other medical imaging device such as a real time ultrasound imaging system.

In the fourth step, the operator may maneuver the operable member 119 through the elongate device 15 to break thrombus around the first distal port or the second distal port. The operator may apply other material such as urethane on the operable member 119 to improve the performance of the operable member. The operator may further apply other material such as urethane within the third lumen 50 or on the elongate device 15 to maintain the patency of the third lumen 50. The operator may further control the operable member 119 to collect the broken thrombus and remove it from the blood vessel.

In the final step, after the thrombus is removed, the operator may disconnect the elongate device 15 from the operable member 119 and leave the operable member 119 on the connector device 18. Then the operator may remove the elongate device 15 from the third lumen 50. If necessary, the operator may remove the operable member 119 from the blood vessel for cleaning or other purposes.

Figure 7:
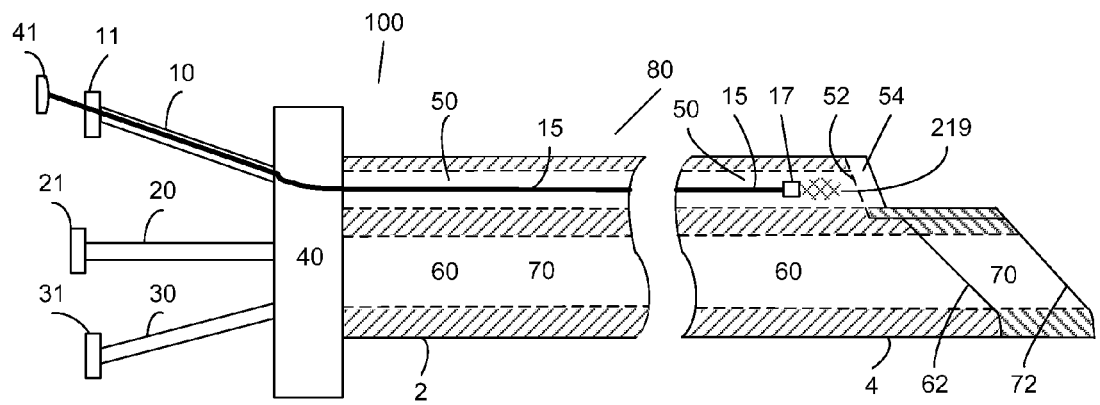
FIG. 7 is a side view of a three-lumen hemodialysis catheter with an expandable brush.
Figure 8:
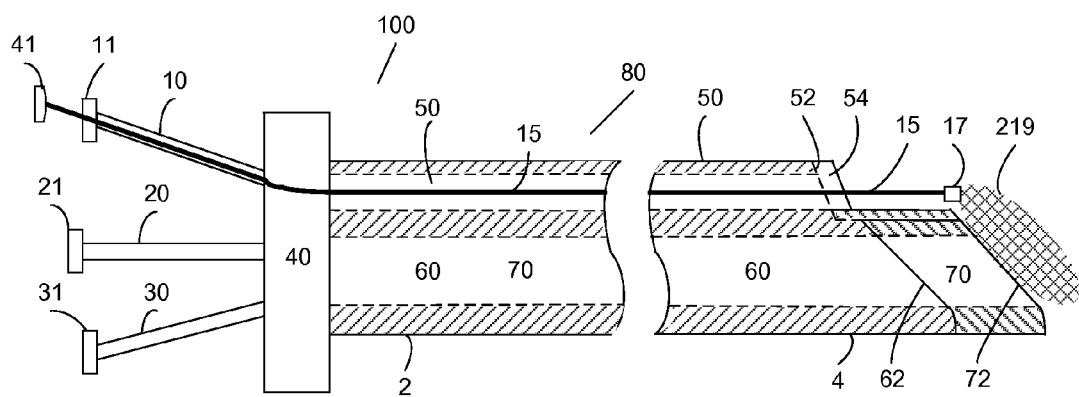
FIG. 8 is a side view of the three-lumen hemodialysis catheter of FIG. 7 illustrating the expanded brush removing clots outside of the first and second lumen.

Referring now to FIGS. 7-8, a third embodiment of the three-lumen catheter 100 for hemodialysis treatment is described. The difference between the third embodiment and the second embodiment is the operable member 219. The operable member 219 may be a brush like device with stiff bristles made of non-metal material. The bristles may collapse when disposed within the third lumen as shown in FIG. 7. The bristles may stick out when emerged from the third lumen as shown in FIG. 8. The device 17 may comprise a controller to control the bristles to act as desired by the operator. The operator may rotate or spin the operable member 219 to remove clots or thrombus. The operator may further control the bristles to extend perpendicularly or angling backward on the operable member 219.

The operable member 219 may be rigid or flexible as desired. The operable member 219 may be made from plastic or metal. For example, the operable member 219 may be made from a metal alloy such as Nitinol. If made from Nitinol, the shape of the operable member 219 can be curved so that when it is extended outside the catheter, the loop would be angled approximately 90 degrees so as to engage the surface of the catheter. The operable member 219 may also be manufactured from a plastic material, e.g., PEBAX, nylon, Hytrel, Arnitel or other polymers, which may be suitable for use during an interventional procedure. If the operable member 219 is made from flexible material, the operable member 219 may be inflated or deflated by an operator though the device 17.

Additionally, or alternatively, the operable member 219 may comprise therapeutic agents to improve the performance and efficiency of removing clots, thrombus or other undesired material.

While various embodiments of the invention have been described, it will be apparent to those of ordinary skill in the art that many more embodiments and implementations are possible within the scope of the invention. The different aspects of the described embodiments may be combined together to improve the performance of the hemodialysis catheter. Accordingly, the invention is not to be restricted except in light of the attached claims and their equivalents. Moreover, the advantages described herein are not necessarily the only advantages of the invention and it is not necessarily expected that every embodiment of the invention will achieve all of the advantaged described.

What is claimed is:

1. A hemodialysis catheter comprising:
   an elongate shaft comprising a plurality of lumens;
   a first lumen of the plurality of lumens having a first distal port, the first lumen being configured for the flow of a fluid in a first direction;
   a second lumen of the plurality of lumens having a second distal port proximal to the first distal port, the second lumen being configured for the flow of the fluid in a second direction opposite to the first direction;
   a third lumen of the plurality of lumens having a third distal port proximal to the second distal port; and
   an elongate device movably disposed through the third lumen, the elongate device having an operable member on a distal end thereof, the operable member configured to directly engage and remove thrombus mechanically from an exterior surface on the elongate shaft near one of the first and second distal ports.

2. The hemodialysis catheter of claim 1 wherein the operable member is a loop.

3. The hemodialysis catheter of claim 1 wherein the operable member is a hoop.

4. The hemodialysis catheter of claim 1 wherein the operable member is a snare.

5. The hemodialysis catheter of claim 1 wherein the operable member is a brush-like device.

6. The hemodialysis catheter of claim 1 wherein the operable member is a balloon.

7. The hemodialysis catheter of claim 1 wherein the third distal port has a movable cover disposed thereover.

8. A hemodialysis catheter comprising:
   an elongate shaft comprising a plurality of lumens;
   a first lumen of the plurality of lumens having a first distal port, the first lumen being configured for the flow of a fluid in a first direction;
   a second lumen of the plurality of lumens having a second distal port proximal to the first distal port, the second lumen being configured for the flow of the fluid in a second direction opposite to the first direction;
   a third lumen of the plurality of lumens having a third distal port proximal to the second distal port; and
   an elongate device disposed through the third lumen, the elongate device having an operable member on a distal end thereof, the operable member configured to engage and remove thrombus from an exterior surface on the elongate shaft near one of the first and second distal ports, wherein third distal port has a movable cover disposed thereover and the movable cover comprises a valve like structure.

9. A method for removing thrombus or clots during a hemodialysis treatment, the method comprising:

providing a hemodialysis catheter having (i) an elongate shaft comprising a plurality of lumens; (ii) a first lumen of the plurality of lumens having a first distal port; (iii) a second lumen of the plurality of lumens having a second distal port proximal to the first distal port; (iv) a third lumen of the plurality of lumens having a third distal port proximal to the second distal port; and (v) an elongate device movably disposed through the third lumen, the elongate device having an operable member on a distal end thereof, the operable member configured to directly engage and remove thrombus mechanically from an exterior surface on the elongate shaft, advancing the operable member distally from the third port to a location near one of the first distal port and the second distal port;

manipulating the operable member so as to break up any thrombus disposed about one of the first distal port and the second distal port.

10. The method of claim 9, further comprising removing the elongate device from the third lumen.

11. The method of claim 9, further comprising applying urethane to the third lumen during the hemodialysis treatment.

* * * * *